United States Patent

Mestre et al.

[11] Patent Number: 4,665,076
[45] Date of Patent: May 12, 1987

[54] PHARMACOLOGICALLY ACTIVE PIPERIDINE DERIVATIVES AND THEIR USE

[75] Inventors: Michel Mestre, Paris; Christian Renault, Taverny, both of France

[73] Assignee: Rhone-Poulenc Sante, Courbevoie, France

[21] Appl. No.: 709,066

[22] Filed: Mar. 6, 1985

[30] Foreign Application Priority Data

Mar. 9, 1984 [FR] France .................. 84 03669

[51] Int. Cl.[4] .................. A61K 31/505; C07D 401/06
[52] U.S. Cl. ..................... 514/259; 514/307; 514/319; 544/283; 546/139; 546/205; 546/146
[58] Field of Search ................ 544/283; 546/139, 146, 546/205; 514/259, 307, 319

[56] References Cited

U.S. PATENT DOCUMENTS

| | | | |
|---|---|---|---|
| 3,149,116 | 9/1964 | Binder et al. | 546/139 |
| 3,795,677 | 3/1974 | Carr et al. | 546/205 |
| 3,857,847 | 12/1974 | Gutzwiller et al. | 546/139 |
| 4,246,268 | 1/1981 | Carr | 546/205 |

FOREIGN PATENT DOCUMENTS 0012643 6/1980 European Pat. Off. .

OTHER PUBLICATIONS

Clemo et al., J. Chem. Soc. 1954 Part III pp. 95-99.
Rubtsov et al. Chem. Abs. 1955 49 332c.

Primary Examiner—Glennon H. Hollrah
Assistant Examiner—James H. Turnipseed
Attorney, Agent, or Firm—Stevens, Davis, Miller & Mosher

[57] ABSTRACT

The piperidine derivatives of formula:

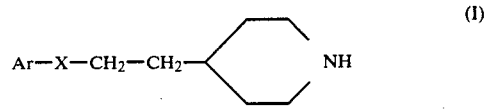

(I)

in which X denotes —CO—, —CHOH— or —CH(NH$_2$)— and Ar denotes

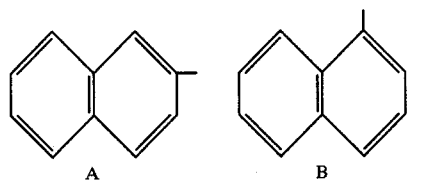

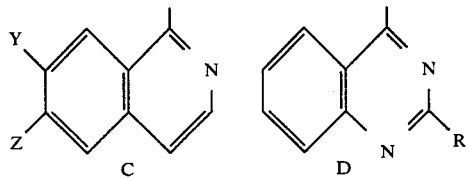

in which R denotes hydrogen or alkyl of 1 to 4 carbon atoms, and Y and Z, which may be identical or different, each denote a hydrogen atom or alkoxy of 1 to 3 carbon atoms, and their addition salts with pharmaceutically acceptable inorganic or organic acids are useful for treating and/or preventing disturbances of cardiac rhythm. These compounds are new except when X is —CO— and Ar is 1-naphthyl or 1-isoquinolyl.

24 Claims, No Drawings

PHARMACOLOGICALLY ACTIVE PIPERIDINE DERIVATIVES AND THEIR USE

The piperidine derivatives of formula:

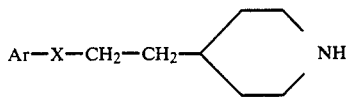
(I)

in which X denotes —CO—, —CHOH— or —CH(NH$_2$)— and Ar denotes an aromatic residue of the formula:

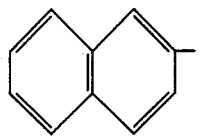
A

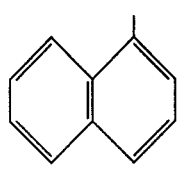
B

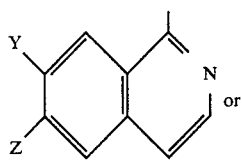
C

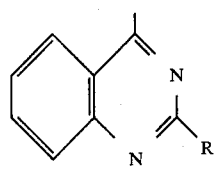
D in which R denotes hydrogen or alkyl of 1 to 4 carbon atoms, Y and Z, which may be identical or different, each denote hydrogen or alkoxy of 1 to 3 carbon atoms, and their addition salts with pharmaceutically acceptable inorganic or organic acids are useful for treating and/or preventing disturbances of cardiac rhythm.

The compounds of formula (I) in which X denotes —CO— and Ar denotes 1-naphthyl or 1-isoquinolyl have already been described (N. V. Rubtsov, Zhur, obshchei. Khim. 1953, 23, 1893 and G. R. Clemo, J. Chem. Soc. 1954, 95), but no pharmacological property or therapeutic application has been indicated for them. The other compounds of formula (I) are new. These are the compounds of formula (I) in which either X denotes —CHOH— or —CH(NH$_2$)— and Ar denotes an aromatic residue of the formula A, B, C or D as defined above, or X denotes —CO— and Ar denotes an aromatic residue of the formula A, C and D mentioned above, except that Y and Z cannot both denote hydrogen, and the salts of these compounds with inorganic or organic acids.

As examples of salts, there may be mentioned hydrochlorides, sulphates, nitrates, phosphates, acetates, propionates, succinates, benzoates, fumarates, maleates, methanesulphonates and salicylates.

Compounds of formula (I) in which X denotes a —CO— group can be prepared by condensing an ester of formula:

(II)

in which R$_1$ is lower alkyl, e.g. methyl or ethyl, and Ar is as hereinbefore defined, with an ester of (4-piperidyl)-propionic acid of formula:

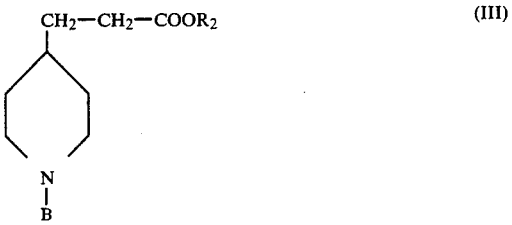
(III)

in which R$_2$ is lower alkyl, and B denotes a group which protects the amine group, and which is stable in anhydrous alkaline medium and capable of being removed in acidic medium, followed by hydrolysis and decarboxylation of the compound of formula:

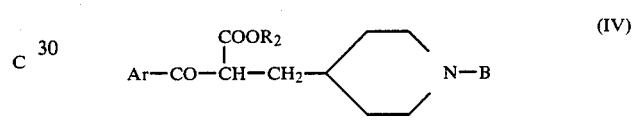
(IV)

thus obtained.

The protective group B may be, for example, one of those described by R. A. BOISSONNAS, Advances in Organic Chemistry 3, page 159, Interscience (1963); advantageously, a benzoyl or benzyloxycarbonyl group is used.

The condensation reaction may be performed in the manner described in "The acetocetic acid ester condensation", C. R. HAUSER et al., Organic Reactions, vol. 1, page 266, Wiley and Sons, 1942. It is advantageous to work in the presence of a base such as an alcoholate, e.g. potassium tert-butylate, or a metal hydride such as sodium hydride or potassium hydride, in an inert solvent such as a hydrocarbon or an aprotic solvent such as tetrahydrofuran, at a temperature from 0° C. to the boiling point of the solvent used.

The hydrolysis reaction may be performed in the way described in "Cleavage of β-keto esters", R. B. WAGNER and H. D. ZOOK, Synthetic Organic Chemistry, page 327, Wiley and Sons, 1953. The most advantageous method consists in heating the product of formula (IV) to boiling in an aqueous solution of an acid such as hydrochloric acid or sulphuric acid.

The compounds of formula (I) in which X denotes —CHOH— can be prepared by reducing the corresponding compounds of formula (I) in which X denotes —CO—.

An appropriate method of reduction consists in using as reducing agent a reducing metal hydride such as one of those mentioned in "Complex hydrides and related reducing agents in organic synthesis", A. HAJOS, Elsevier Scientific Publishing Company, Amsterdam, Oxford, New York 1979. Suitable reducing agents include alkali metal borohydrides such as sodium borohydride or potassium borohydride which are used to room temperature in a solvent such as an alcohol, e.g. methanol or ethanol, a water/alcohol mixture or tetrahydrofuran, or lithium aluminium hydride which is used in an inert solvent such as ether, tetrahydrofuran or a hydrocarbon at a temperature from 0° C. to the boiling point of the solvent.

The compounds of formula (I) in which X denotes —CH(NH$_2$)— can be prepared from the compounds of formula (I) in which X denotes —CO— by the methods described by C. A. BUEHLER AND D. E. PEARSON, Survey of Organic Synthesis, vol. 1, page 427, Wiley Interscience 1970. An especially advantageous process consists in treating the ketone compound with ammonium formate at a temperature from 150° to 200° C., and then hydrolysing the product in acid medium.

The reaction mixture obtained in the aforesaid processes may be worked up by conventional physical methods (e.g. evaporation, extraction, distillation, crystallisation, chromatography, etc.) or chemical methods (e.g. salt formation and regeneration of the base, etc.) in order to isolate the compounds of formula (I) in the pure state, either in the form of the free base or in the form of a salt of the latter with an inorganic or organic acid.

The Examples which follow illustrate the preparation of the compounds of formula (I).

EXAMPLE 1

1-(2-Naphthyl)-3-(4-piperidyl)-1-propanone

To ethyl 2-naphthoate (5.5 g) and a 20% suspension of potassium hydride in oil (10 ml) in boiling anhydrous tetrahydrofuran (25 ml), there is added, under nitrogen, a solution of ethyl 3-(1-benzoyl-4-piperidine)-propionate (7 g) in anhydrous tetrahydrofuran (25 ml). After 20 hours of boiling, the mixture is cooled, ethanol (5 ml) is added, and the solvents are removed under reduced pressure.

To the residue is added water (50 ml), 11N hydrochloric acid (50 ml) and acetic acid (50 ml) and the mixture is boiled for 8 hours. The mixture is then cooled, and diluted with water. The aqueous phase is washed with ether, made alkaline with 12N sodium hydroxide solution and extracted with ether (2×200 ml).

The ether phase is washed with water, dried over anhydrous magnesium sulphate and evaporated to dryness under reduced pressure. A crude product (2.7 g) is obtained which is taken up in ethanol (20 ml) to which ethereal hydrogen chloride is added. The precipitated hydrochloride is filtered off, washed and dried. 1-(2-Naphthyl)-3-(4-piperidyl)-1-propanone (2.5 g) is obtained in the form of hydrochloride, m.p. 225° C.

EXAMPLE 2

1-(1-Naphthyl)-3-(4-piperidyl)-1-propanone

To a mixture, under nitrogen, of a 50% suspension of potassium hydride in oil (8 ml) and anhydrous tetrahydrofuran (25 ml), ethyl 1-naphthoate (3 g) is added and the mixture is brought to reflux. A solution of ethyl 3-(1-benzoyl-4-piperidine)propionate (2.9 g) dissolved in tetrahydrofuran (25 ml) is then added. The mixture is refluxed for 5 hours and cooled. A little ethanol is added and the reaction medium is evaporated to dryness. The residue is taken up in 6N hydrochloric acid (50 ml) and ethanol (25 ml) and is refluxed again for 36 hours. The reaction medium is washed with ether, made alkaline with 12N sodium hydroxide solution, and extracted with ethyl acetate. The organic phase is washed with water, dried over magnesium sulphate and evaporated to dryness under reduced pressure. The product (1.54 g) is obtained in the form of an oil which is converted to the hydrochloride in acetone. 1-(1-Naphthyl)-3-(4-piperidyl)-1-propanone is obtained as the hydrochloride, m.p. 171° C.

EXAMPLE 3

1-(6,7-Dimethoxy-1-isoquinolyl)-3-(4-piperidyl)-1-propanone

To sodium hydride (14 g) in anhydrous tetrahydrofuran (200 ml), a solution of ethyl 6,7-dimethoxy-1-isoquinolinecarboxylate (40.8 g) and ethyl 3-(1-benzoyl-4-piperidine)propionate (37.7 g) in anhydrous tetrahydrofuran (250 ml) is added. The mixture is boiled under reflux for 4 hours, cooled to 0° C., and then hydrolysed with 6N hydrochloric acid (90 ml). The tetrahydrofuran is evaporated under reduced pressure, 6N hydrochloric acid (200 ml) is added and the mixture is again boiled under reflux for 18 hours. The aqueous phase is washed with ether (2×100 ml), made alkaline with concentrated ammonia (150 ml) and extracted several times with chloroform. The chloroform phase is washed with water, dried over magnesium sulphate and evaporated to dryness under reduced pressure. A product (45 g) is obtained which is chromatographed on silica gel using a chloroform/diethylamine (9:1) mixture as eluant. A product (30 g) is obtained which is dissolved in ethanol (200 ml). The solution is brought to pH 1 with an ethanolic solution of hydrogen chloride. Acetone (200 ml) is added, and induces crystallisation of the product. After filtration, washing the crystals in acetone and ether and drying, 1-(6,7-dimethoxy-1-isoquinolyl)-3-(4-piperidyl)-1-propanone (15 g) is obtained as the hydrochloride, m.p. 228° C.

Ethyl 6,7-dimethoxy-1-isoquinolinecarboxylate can be prepared by the method of T. KAMETANI et al., Chem. Abs. 1967, 66, 28632μ.

EXAMPLE 4

1-[2-(1,1-Dimethylethyl)-4-quinazolinyl]-3(4-piperidyl)-1-propanone

Under nitrogen, sodium hydride (6.5 g., as an 80% suspension in oil) is mixed with anhydrous tetrahydrofuran (60 ml). The mixture is stirred and a solution of ethyl 2-(1,1-dimethylethyl)-4-quinazolinecarboxylate (22.4 g) in anhydrous tetrahydrofuran (150 ml) is added. The mixture is stirred for 30 minutes and a solution of ethyl 3-(1-benzoyl-4-piperidine)propionate (12.6 g) in anhydrous tetrahydrofuran (100 ml) is added. The mixture is stirred for 20 hours at room temperature. Ethanol (50 ml) is then added and the solvent is evaporated under reduced pressure. The residue is taken up in water and the aqueous phase extracted 4 times with ethyl acetate. The organic phase is dried over anhydrous magnesium sulphate and evaporated to dryness. A product (29 g) is obtained which is taken up in ethanol (100 ml) and 6N hydrochloric acid (100 ml). The mixture is also boiled for 50 hours. The ethanol is then evaporated and the residue taken up in methylene chloride and water. The aqueous phase is made alkaline with 12N sodium hydroxide solution. The oil which separates is extracted with methylene chloride and the organic extract is dried over magnesium sulphate and then evaporated to dryness under reduced pressure. A product (17.3 g) is obtained which is chromatographed on silica gel using a chloroform/diethylamine (95:5) mixture as eluant. 1-[2-(1,1-dimethylethyl)-4-quinazolinyl]-3-(4-piperidyl)-1-propanone (8.8 g) is obtained as an oil, the proton NMR spectrum of which in CDCL₃ has the following characteristics:

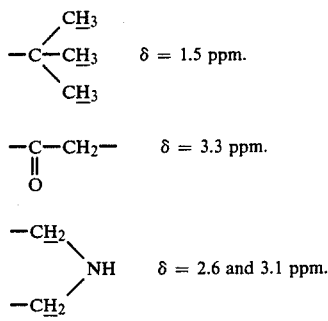

H₅ (quinazolinyl)δ = 8.1 ppm
H₈ (quinazolinyl)δ = 8.7 ppm
H₆ and H₇ (quinazolinyl) = 7.7 and 7.9 ppm.
The remaining protons are between 0.9 and 1.9 ppm.
A sample recrystallised from ethyl ether melts at 127° C.

Ethyl-2-(1,1-dimethylethyl)-4 -quinazolinecarboxylate can be prepared as follows: To aniline (10 g) and triethylamine (16.4 g) in chloroform (80 ml), pivaloyl chloride (19.5 g) is added with cooling. After 3 hours of stirring, water is added and the pH is brought to 10 using sodium hydroxide. The mixture is separated and the aqueous phase extracted with chloroform. The combined organic phases are washed with water, dried over magnesium sulphate and evaporated to dryness under reduced pressure. The residue is taken up in ether, and the solid is filtered off and dried. A product (14.5 g) is obtained to which thionyl chloride (13 ml) is added. The mixture is heated at 90° C. for 3 hours. The excess thionyl chloride is removed by distillation and ethyl cyanoformate (10 ml) and stannic chloride (11.8 ml) are added. The mixture is heated at 130° C. for 10 min. and then cooled. The residue is dissolved in methylene chloride, and the organic phase is washed with water, dried over magnesium sulphate and evaporated to dryness under reduced pressure. The residue is taken up in isopropyl ether (200 ml). Some insoluble material is filtered off and the filtrate is evaporated. A resinous product (18.8 g) is obtained which is chromatographed on silica gel using a cyclohexane/ethyl acetate (9:1) mixture as eluant. Ethyl 2-(1,1-dimethylethyl)-4-quinazolinecarboxylate (17.5 g) is obtained, m.p. 46°–47° C.

EXAMPLE 5

1-(1-Naphthyl)-3-(4-piperidyl)-1-propanol

To 1-(1-naphthyl)-3-(4-piperidyl)-1-propanone (12 g) in methanol (200 ml), sodium borohydride (2 g) is added in the course of 30 minutes. After 1 hour of stirring, 5N hydrochloric acid is added until the pH is 3. The mixture is then concentrated to dryness under reduced pressure. The residue is dissolved in water and the aqueous phase is washed with ethyl acetate. The aqueous phase is then made alkaline and extracted with chloroform (3×250 ml). The organic extract is washed with water, dried over magnesium sulphate and evaporated to dryness under reduced pressure. A product (11.5 g) is obtained which is chromatographed on silica gel using a chloroform/diethylamine (9:1) mixture as eluant. The product (7.5 g) is dissolved in acetone, and the solution is treated with ethereal hydrogen chloride. 1-(1-Naphthyl)-3-(4-piperidyl)-1-propanol (5.1 g) is obtained as the hydrochloride, m.p. 165° C.

EXAMPLE 6

1-(1-Isoquinolyl)-3-(4-piperidyl)-1-propanol

To 1-(1-isoquinolyl)-3-(4-piperidyl)-1-propanone (11.8 g) in ethanol (120 ml), sodium borohydride (1.2 g) is added portionwise and with cooling. After 2 hours, the solvent is evaporated under reduced pressure. The residue is taken up in water (200 ml), acidified to pH 2 with hydrochloric acid, and the solution is then made alkaline with 12N sodium hydroxide solution. The oil which separates is extracted with ethyl acetate (3×200 ml). The organic phase is washed with water, dried over magnesium sulphate and evaporated to dryness under reduced pressure. The residue is recrystallised from acetone. A product (6 g) is obtained which is converted to the hydrochloride in ethanol. After recrystallisation from ethanol, 1-(1-isoquinolyl)-3-(4-piperidyl)-1-propanol (2 g) is obtained as the dihydrochloride, m.p. 210° C.

1-(1-Isoquinolyl)-3-(4-piperidyl)-1-propanone can be prepared by the method of G. R. CLEMO et al., J. Chem. Soc. 1954, 95.

EXAMPLE 7

1-(6,7-Dimethoxy-1-isoquinolyl)-3-(4-piperidyl)-1-propanol

To 1-(6,7-dimethoxy-1-isoquinolyl)-3-(4-piperidyl)-1-propanone (5 g) in methanol (100 ml), sodium borohydride (1.2 g) is added at room temperature. After 20 minutes, the solvent is removed under reduced pressure, and the residue is taken up in water and chloroform. The organic phase is washed with water, dried over magnesium sulphate and evaporated to dryness under reduced pressure. A product (5 g) is obtained which is dissolved in ethanol (50 ml). Ethanolic hydrogen chloride is added until the pH equals 1 followed by acetone (100 ml). After crystallisation, the crystals are filtered off and washed with acetone and then ether. After being dried, 1-(6,7-dimethoxy-1-isoquinolyl)-3-(4-piperidyl)-1-propanol (4.4. g) is obtained as the dihydrochloride, m.p. 192° C.

EXAMPLE 8

1[2-(1,1-Dimethylethyl)-4-quinazolinyl]-3-(4-piperidyl)-1-propanol

To ethanol (100 ml), sodium hydroxide pellets (2 g), 1-[2-(1,1-dimethylethyl)-4-quinazolinyl]-3-(4-piperidyl)-1-propanone acetate (7.6 g) and sodium borohydride (0.8 g), are added. After 2 hours of stirring, the ethanol is removed under reduced pressure and the residue is taken up in water and ethyl acetate. The organic phase is washed with water, dried over magnesium sulphate and evaporated to dryness under reduced pressure. A product (5.6 g) is obtained which is chromatographed on silica gel with a chloroform/diethylamine (97:3) mixture as eluant. The product (3.6 g) is collected and recrystallised from a petroleum ether/ethyl acetate mixture. 1-[2-(1,1-Dimethylethyl)-4-quinazolinyl)-3-(4-piperidyl)-1-propanol (1.6 g) is obtained, m.p. 110° C.

EXAMPLE 9

1-(2-Naphthyl)-3-(4-piperidyl)-1-propanamine

A mixture of 1-(2-naphthyl)-3-(4-piperidyl)-1-propanone (8.2 g) and ammonium formate (19 g) is heated at 100° C. for 7 hours. The residue is taken up in chloroform and chromatographed on silica gel with a toluene/ethanol/diethylamine (15:2:1) mixture as eluant. A product (7.2 g) is recovered which is boiled with 6N hydrochloric acid (70 ml) and acetic acid (20 ml) for 22 hours. After cooling, the reaction medium is made alkaline with a 12N sodium hydroxide solution, and the oil which separates out is extracted with methylene chloride. The organic phase is washed with water, dried over magnesium sulphate and evaporated to dryness under reduced pressure. The dihydrochloride is formed in isopropanol and recrystallised from n-propanol. 1-(2-Naphthyl)-3-(4-pipeeridyl)-1-propanamine (2.5 g) is obtained as the dihydrochloride, m.p. 260° C.

EXAMPLE 10

1-(1-Isoquinolyl)-3-(4-piperidyl)-1-propanamine

A mixture of 1-(1-isoquinolyl)-3-(4-piperidyl)-1-propanone (2.5 g) and ammonium formate (7.5 g) is heated to 160° C. for 5 hours. The mixture is cooled, water (100 ml) is added, and the insoluble material is extracted with ethyl acetate (3×50 ml). After the solvent has been evaporated, the residue is taken up in 6N hydrochloric acid (35 ml) and boiled for 1 hour. The mixture is diluted with water (100 ml), the pH of the aqueous mixture is adjusted to 7, and the solution is extracted with ethyl acetate. The aqueous phase is made alkaline to pH 11, and extracted again with chloroform (3×100 ml). The organic phase is dried over magnesium sulphate and evaporated to dryness under reduced pressure. 1-(1-Isoquinolyl)-3-(4-piperidyl)-1-propanamine (0.13 g) is obtained, the proton NMR spectrum of which is deuterated chloroform has the following characteristics:

$H_3\delta$ = 8.5 ppm, $H_{4\ 5,6,7}\delta$ = between 7.5 and 8 ppm.

$H_8\delta$ = 8.1 ppm,

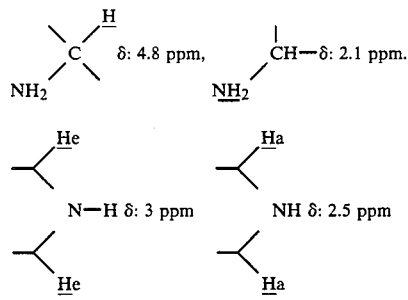

The pharmacological properties of the compounds of formula I have been demonstrated in the following test for antiarrhythmic activity.

The antiarrhythmic activity of the compounds of formula (I) was demonstrated by means of the aconitine test in rats. The principle of the technique rests on the time required for inducing ventricular arrhythmias with aconitine slowly perfused in rats. An antiarrhythmic substance delays the appearance of the arrhythmia, and this delay is proportional to the activity of the substance.

Groups of 5 male rats are used. Individual anaesthetisation is carried out (10% urethane: 1 g/kg/ip) to permit catheterisation of the vein of the penis. The electrocardiogram is recorded. At time T=O, the substance studied is injected as an aqueous solution, in the proportion of 2.5 ml of solution per kg, in the course of 30 seconds. At time T=60 seconds, or 30 seconds after completing the injection, aconitine is perfused at the rate of 20 μg per minute until supraventricular extrasystoles appear. The perfusion time of the aconitine is noted. The results are expressed as an $ED_{50}$, i.e. the dose of the product under test in mg/kg which increases by 50% the perfusion time of aconitine relative to control animals.

The results obtained are collated in the Table below:

| PRODUCT OF | ACONITINE TEST (rat) $ED_{50}$ mg/kg i.v. |
| --- | --- |
| Example 1 | 4 |
| Example 2 | 3.8 |
| Example 3 | 2.1 |
| Example 5 | 1.42 |
| Example 6 | 2.7 |
| Example 7 | 2.5 |
| Example 8 | 1 |
| Example 9 | <0.3 |
| Quinidine | 7.5 |

The compounds of formula (I) thus have outstanding antiarrhythmic properties and are more active than quinidine.

The acute toxicities of the compounds of formula (I) were determined by intravenous administration to male $CD_1$ mice (Charles RIVER). The $LD_{50}$ values, calculated after 3 days of observation by the cumulative method of J. J. REED and H. MUENCH (Amer. J. Hyg., 27, 493, 1938), are greater than 15 mg/kg i.v.

The compounds of formula I and their pharmaceutically acceptable acid addition salts can be used in human therapy for treating and/or preventing disturbances of cardiac rhythm.

For this purpose, they may be used in the form of pharmaceutical compositions comprising, as active ingredient, a piperidine derivative of formula I, or a pharmaceutically acceptable acid addition salt thereof. In these compositions the active ingredient may be in association with a compatible pharmaceutically acceptable diluent, adjuvant or coating which is a solid, or semi-solid, a liquid containing a sweetener, flavouring, thickener, colorant, stabilizer and/or wetting agent, or a sterile injectable liquid. Such compositions may normally contain 1 to 95% by weight of the active ingredient. The compositions of the invention may be given by oral (including sub-lingual), parenteral, or rectal administration.

Solid compositions for oral administration may be tablets, pills, powders (particularly in gelatin capsules or cachets) or granules. In these compositions, the active compound of the invention may be mixed with one or more inert diluents such as starch, cellulose, sucrose, lactose or silica. These compositions may also contain substances other than diluents, for example one or more lubricants such as magnesium stearate or talc, a colorant, a coating (coated tablets), or a varnish.

Liquid compositions for oral administration may be solutions, suspensions, emulsions, syrups and pharmaceutically acceptable elixirs containing inert diluents such as water, ethanol, glycerol, vegetable oils or paraffin oils. These compositions may contain substances other than diluents, for example wetting agents, sweeteners, thickeners, flavourings, colorants or stabilisers.

Sterile compositions for parenteral administration are preferably aqueous or non-aqueous solutions, suspensions or emulsions. The solvent or vehicle may be, for example, water, propylene glycol, polyethylene glycol, a vegetable oil, especially olive oil, an injectable organic ester, for example ethyl oleate, or other suitable organic solvent. These compositions may also contain adjuvants, in particular wetting agents, isotonising agents, emulsifiers, dispersants and stabilisers. Sterilisation may be carried out in various ways, for example by asepticising filtration, by incorporating sterilising agents in the composition, by irradiation or by heating. The compositions may also be prepared in the form of sterile solid compositions which may be dissolved at the time of use in an injectable sterile medium.

The compositions for rectal administration may be suppositories or rectal capsules which, in addition to the active product, contain a semi-solid excipient such as cocoa butter, a semi-synthetic glyceride or a polyethylene glycol.

The dosage depends on the effect sought, the condition of the patient and the administration route used. For example, for oral administration to an adult of about 70 kg, it can range from 50 to 800 mg of active substance per 24 hours, each unit dose containing from 10 100 mg of the active ingredient.

The examples which follow illustrate compositions according to the invention.

EXAMPLE A

An injectable solution containing 10 mg of active product and having the following composition is prepared by the usual technique.

| 1-[2-(1,1-dimethylethyl)-4 quinazolinyl]-3 (4-piperidyl)-1 | |
|---|---|
| propanol | 10 mg |
| N hydrochloric acid | 0,0375 ml |
| Ascorbic acid | 1 mg |
| Mannitol | 245 mg |
| Water q.s. | 5 ml. |

EXAMPLE B

Tablets containing 25 mg of active ingredient and having the following composition are prepared by the usual technique.

| 1-[2-(1,1-dimethylethyl)-4 quinazolinyl]-3 (4-piperidyl)-1 | |
|---|---|
| propanol | 25 mg |
| Lactose | 52 mg |
| Cellulose | 20 mg |
| Polyvidone excipient | 5 mg |
| Sodium carboxymethylstarch | 11 mg |
| Talc | 5 mg |
| Magnesium stearate | 1 mg |
| colloidal silica | 1 mg |
| Hydroxy propyl methylcellulose - glycerine and titanium oxide in suspension q.s. | 123 mg |

EXAMPLE C

Gelatin capsules containing 50 mg of active indredient and having the following composition are prepared by the usual technique.

| 1-[2-(1,1-dimethylethyl)]-4 quinazolinyl]-3(4-piperidyl)-1 | |
|---|---|
| Propanol | 50 mg |
| Lactose | 104 mg |
| Cellulose | 40 mg |
| Polyvidone excipient | 10 mg |
| Sodium carboxymethylstarch | 22 mg |
| Talc | 10 mg |
| Magnesium stearate | 2 mg |
| Colloidal silica | 2 mg |

We claim:

1. A pharmaceutical composition useful for treating disturbances of cardiac rhythm comprising, as active ingredient, an effective amount of a piperidine derivative of formula:

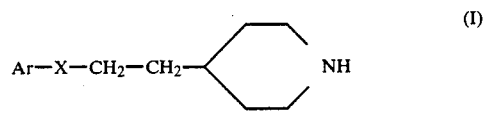

in which either X denotes —CHOH— or —CH(NH$_2$)— and Ar denotes an aromatic residue of the formula:

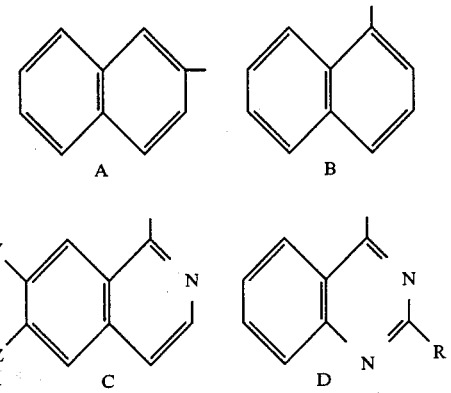

in which R denotes hydrogen or alkyl of 1 to 4 carbon atoms, and Y and Z, which may be identical or different, each denote hydrogen or alkoxy of 1 to 3 carbon atoms, or X denotes —CO— and Ar denotes an aromatic residue of the formula A, B, C or D as defined above except that Y and Z cannot both denote hydrogen, or a pharmaceutically acceptable acid addition salt of such a compound, in association with a compatible pharmaceutically acceptable diluent, adjuvant, or coating which is a solid or semi-solid, a liquid containing a sweetener, flavouring, thickener, colorant, stabilizer and/or wetting agent, or a sterile injectable liquid.

2. A composition according to claim 1 in the form of a tablet, sugar-coated pill, capsule, or suppository.

3. A composition according to claim 1 containing 1 to 90% by weight of the said active ingredient.

4. A composition according to claim 1 in which the active ingredient is 1-(2-naphthyl)-3-(4-piperidyl)-1-propanone or a pharmaceutically acceptable acid addition salt thereof.

5. A composition according to claim 1 in which the active ingredient is 1-(1-naphthyl)-3-(4-piperidyl-1-propanone or a pharmaceutically acceptable acid addition salt thereof.

6. A composition according to claim 1 in which the active ingredient is 1-(6,7-dimethoxy-1-isoquinolyl)-3-(4-piperidyl)-1-propanone or a pharmaceutically acceptable acid addition salt thereof.

7. A composition according to claim 1 in which the active ingredient is 1-[2-(1,1-dimethylethyl)-4-quinazolinyl]-3-(4-piperidyl)-1-propanone or a pharmaceutically acceptable acid addition salt thereof.

8. A composition according to claim 1 in which the active ingredient is 1-(1-naphthyl)-3-(4-piperidyl)-1-propanol or a pharmaceutically acceptable acid addition salt thereof.

9. A composition according to claim 1 in which the active ingredient is 1-(1-isoquinolyl)-3-(4-piperidyl)-1-propanol or a pharmaceutically acceptable acid addition salt thereof.

10. A composition according to claim 1 in which the active ingredient is 1-(6,7-dimethoxy-1-isoquinolyl)-3-(4-piperidyl)-1-propanol or a pharmaceutically acceptable acid addition salt thereof.

11. A composition according to claim 1 in which the active ingredient is 1-[2-(1,1-dimethylethyl)-4-quinazolinyl]-3-(4-piperidyl)-1-propanol or a pharmaceutically acceptable acid addition salt thereof.

12. A composition according to claim 1 in which the active ingredient is 1-(2-naphthyl)-3-(4-piperidyl)-1-propanamine or a pharmaceutically acceptable acid addition salt thereof.

13. A composition according to claim 1 in which the active ingredient is 1-(1-isoquinolyl)-3-(4-piperidyl)-1-propanamine or a pharmaceutically acceptable acid addition salt thereof.

14. A piperidine derivative of the formula:

$$Ar-X-CH_2-CH_2-\langle\text{piperidine}\rangle NH \quad (I)$$

in which either X denotes —CHOH— or —CH(NH$_2$)— and Ar denotes an aromatic residue of the formula:

[Structures A and B: naphthyl groups]

[Structures C and D: isoquinolinyl and quinazolinyl groups with Y, Z, R substituents]

in which R denotes hydrogen or alkyl of 1 to 4 carbon atoms, and Y and Z, which may be identical or different, each denote hydrogen or alkoxy of 1 to 3 carbon atoms, or X denotes —CO— and Ar denotes an aromatic residue of the formula A, C or D as defined above, except that Y and Z cannot both denote hydrogen, and its salts with pharmaceutically acceptable acids.

15. A compound according to claim 14 which is 1-(2-naphthyl)-3-(4-piperidyl)-1-propanone and its pharmaceutically accepting acid addition salts.

16. A compound according to claim 14 which is 1-(6,7-dimethoxy-1-isoquinolyl)-3-(4-piperidyl)-propanone and its pharmaceutically acceptable acid addition salts.

17. A compound according to claim 14 which is 1-[2-(1,1-dimethylethyl)-4-quinazolinyl]-3-(4-piperidyl)-1-propanone and its pharmaceutically acceptable acid addition salts.

18. A compound according to claim 14 which is 1-(1-naphthyl)-3-(4-piperidyl)-1-propanol and its pharmaceutically acceptable acid addition salts.

19. A compound according to claim 14 which is 1-(1-isoquinolyl)-3-(4-piperidyl)-1-propanol and its pharmaceutically acceptable acid addition salts.

20. A compound according to claim 14 which is 1-(6,7-dimethoxy-1-isoquinolyl)-3-(4-piperidyl)-1-propanol and its pharmaceutically acceptable acid addition salts.

21. A compound according to claim 14 which is 1-[2-(1,1-dimethylethyl)-4-quinazolinyl]-3-(4-piperidyl)-1-propanol and its pharmaceutically acceptable acid addition salts.

22. A compound according to claim 14 which is 1-(2-napthyl)-3-(4-piperidyl)-1-propanamine and its pharmaceutically acceptable acid addition salts.

23. A compound according to claim 14 which is 1-(1-isoquinolyl)-3-(4-piperidyl)-1-propanamine and its pharmaceutically acceptable acid addition salts.

24. Method of treating cardiac arrhythmia which comprises administering to a subject an effective amount of a piperidine derivative of the formula:

$$Ar-X-CH_2-CH_2-\langle\text{piperidine}\rangle NH \quad (I)$$

as defined in claim 14, or a pharmaceutically acceptable acid addition salt thereof.

* * * * *

UNITED STATES PATENT AND TRADEMARK OFFICE
CERTIFICATE OF CORRECTION

PATENT NO. : 4,665,076
DATED : May 12, 1987
INVENTOR(S) : MESTRE, et al.

It is certified that error appears in the above-identified patent and that said Letters Patent is hereby corrected as shown below:

In the Heading please correct the following:

--[30] Mar. 9, 1984 [FR] France....8403670--.

Signed and Sealed this

Twenty-sixth Day of January, 1988

Attest:

DONALD J. QUIGG

*Attesting Officer*       *Commissioner of Patents and Trademarks*